United States Patent [19]

Gray et al.

[11] 4,176,826
[45] Dec. 4, 1979

[54] SAFETY CATCH APPARATUS FOR A SUSPENSION SYSTEM

[75] Inventors: David A. Gray, Waukesha; Marvin L. Sivertsen, Milwaukee, both of Wis.

[73] Assignee: General Electric Company, Milwaukee, Wis.

[21] Appl. No.: 921,197

[22] Filed: Jul. 3, 1978

[51] Int. Cl.$^2$ .............................................. B66D 1/48
[52] U.S. Cl. .................................... 254/175; 187/89; 188/189
[58] Field of Search .................. 254/139, 178, 190 R, 254/175, 173 R; 187/88, 89, 94, 71, 8.47, 38; 188/134, 180, 188, 189

[56] References Cited

U.S. PATENT DOCUMENTS

| | | | |
|---|---|---|---|
| 3,762,512 | 10/1973 | McIntyre | 188/189 |
| 3,949,842 | 4/1976 | Kiehn | 188/189 |
| 4,078,634 | 3/1978 | Thomas | 187/89 |

*Primary Examiner*—Robert J. Spar
*Assistant Examiner*—Kenneth W. Noland
*Attorney, Agent, or Firm*—Douglas E. Stoner

[57] ABSTRACT

The safety catch apparatus includes a generally vertically supported stationary bar which extends beyond the uppermost and lowermost positions of a suspended member. The suspended member has an aperture adapted to receive the stationary bar. The suspended member also has an inner chamber which communicates with the aperture. A catch block is sized to fit within the chamber and is adapted for vertical movement within the chamber. The catch block also includes a vertical slot which is adapted for slideable engagement with the stationary bar. A suspension system is connected to the suspended member so that the suspended member and the constrained catch block jointly move along the stationary bar. The vertical slot of the catch block has open recesses in the opposite sides and each recess has a base and an inner wall angulated toward the slot. A roller freely rests in the base of each recess adjacent to, but not in contact with, the stationary bar. The apparatus includes an activation mechanism which automatically generates relative motion between the roller and the catch block in the event of a suspension system failure. The relative motion will advance each roller along the inner wall of the recess, whereby each roller becomes wedged between the inner wall of the catch block and the stationary bar. The stationary bar will thus immediately support the suspended member in the event of a failure of the suspension system.

9 Claims, 6 Drawing Figures

SAFETY CATCH APPARATUS FOR A SUSPENSION SYSTEM

BACKGROUND OF THE INVENTION

The invention relates generally to an automatic safety catch apparatus for supporting a suspended member in the event that the suspension system fails. The invention relates particularly to suspended members positioned above a person where the safety catch apparatus must positively engage and where the amount of drop of the supported member is extremely critical.

There are numerous devices in which a heavy member is supported by a suspension system and is periodically raised and lowered to positions along a vertical column. A common problem with such devices is that a failure of any portion of the suspension system may allow the suspended member to drop, thereby damaging the member and anything in the path of the dropping member. This problem is particularly critical in devices where the suspension system is positioned above a person. Such devices include suspended X-ray and nuclear imaging equipment. The equipment, weighing approximately four hundred pounds, is suspended directly above and closely to a recumbent patient undergoing analysis. A failure of the suspension system would obviously be critical to the safety of the patient. In addition, due to the close proximity of the suspended weight above the patient, a system having an automatic safety catch which allows a free fall drop of more than one-quarter inch before locked engagement could also be critical to the safety of the patient. Another particular problem with such devices is that often there is only a partial loss of tension of the suspension system which permits a slow drop of the member, but which is insufficient to activate the safety catch. The slightest drop of the heavy suspended weight would be critical to the safety of the patient.

A common prior art safety catch for suspension systems uses a spring to sense a loss of tension and to activate a lug into the teeth of a drive sprocket. These devices typically require from one-half to two inches of free fall drop before locked engagement. If the inital tooth is not engaged, free fall drop continues until the next tooth rotates to the engaging lug. Another common prior art device uses electrical switches and solenoids to engage a brake as a safety catch for a suspension system. Such braking devices have considerable mass which requires time to position and permits a long free fall drop prior to locked engagement.

All such known prior art devices permit drops far exceeding one-quarter inch and are, therefore, not acceptable in critical suspended member systems. The prior art has resorted to expensive threaded lead screw drive systems to position and manipulate the suspended member. The prior art has also resorted to expensively over-designed and redundant suspension systems to assure safe operation of the suspended member.

Accordingly, one object of the present invention is to provide an automatic, positive safety catch apparatus for a suspended member in the event that the suspension system fails.

Another object of the invention is to provide a safety catch apparatus for a suspended member which allows a minimal drop of the member upon failure of the suspension system.

Another object of the invention is to provide a safety catch which will activate upon a partial release in tension of the system.

Another object of the invention is to provide a mechanical safety catch apparatus which is not expensive to produce and install and which does not require complex servicing.

Still a further object of the invention is to provide a safety catch apparatus which can be readily reset after engagement and subsequent repair of the failed suspension system.

SUMMARY OF THE INVENTION

The invention is directed to a safety catch apparatus for retaining a suspended member in the event that the suspension system fails. The apparatus includes a generally vertically supported stationary bar which extends beyond the uppermost and lowermost positions of the suspended member. The suspended member has an aperture adapted to receive the stationary bar. The suspended member also has an inner chamber having an upper and lower surface which communicates with the aperture. A catch block is sized to fit within the chamber and is adapted for vertical movement within the chamber. The catch block also includes a vertical slot which is adapted for slideable engagement with the stationary bar. The suspension system, such as a cable, is connected to the catch block so that the suspended member and the constrained catch block jointly moves along the stationary bar. The vertical slot of the catch block has open recesses in the opposite sides and each recess has a base and an inner wall angulated toward the slot. A roller freely rests in the base of each recess adjacent to, but not in contact with the stationary bar. Actuator springs are interposed between the catch block and the upper surface of the chamber and are compressed once tensile force is applied to the catch block by the suspension system. Actuator pins are interposed between the catch block and the lower surface of the chamber with the pins positioned beneath the base of each of the recesses in the catch block. The catch block has corresponding vertical openings at the base of each recess adapted to receive the pin. Once the tensile force is removed from the catch block, the compressed springs will immediately force the catch block downward over the pins which will advance each roller along the inner wall of the recess, whereby each roller becomes wedged between the inner wall of the catch block and the stationary bar. The stationary bar will thus immediately support the suspended member in the event of a failure of the suspension system.

BRIEF DESCRIPTION OF THE DRAWINGS

While the novel features of the invention are set forth with particularity in the appended claims, the invention will be better understood, along with other features thereof, from the following detailed description taken in conjunction with the drawings in which:

DESCRIPTION OF THE PREFERRED EMBODIMENT

Figure 1:
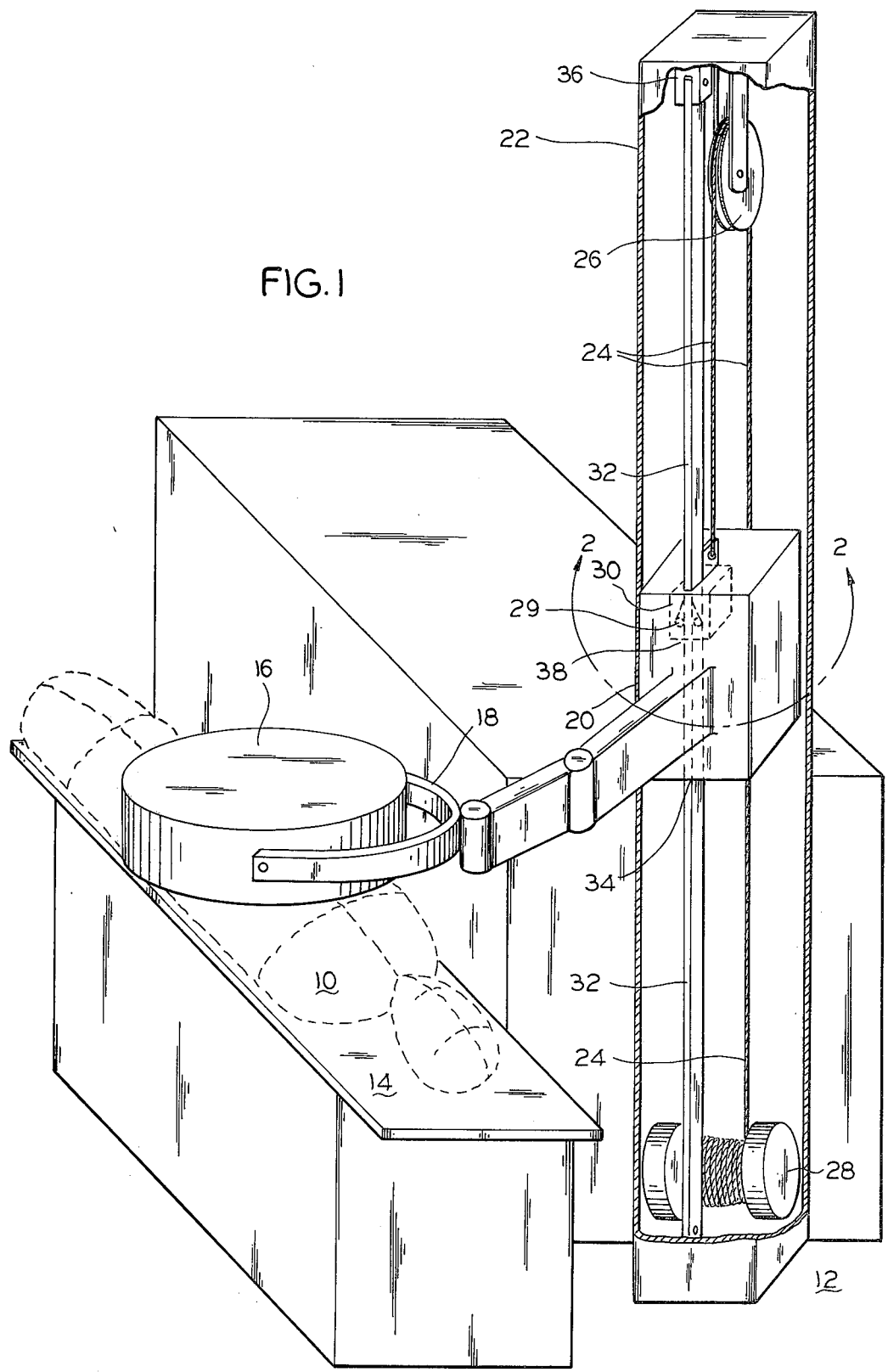
FIG. 1 is a perspective view of a patient undergoing analysis by a suspended nuclear data camera incorporating a safety catch apparatus of the present invention.

Referring first to FIG. 1, there is shown a typical example of where the invention is used. A patient 10 is shown undergoing analysis by a nuclear imaging system 12 while being supported by a table 14. During this particular analysis, the patient 10 receives an internal dose of radiopharmaceutical compounds which emit gamma ray energy. The gamma ray energy is detected by a detector 16 for imaging internal portions of the patient. The detector 16 contains scintillation crystals, photomultiplier tubes, and lead shielding and weighs approximately four hundred pounds. During analysis, the heavy detector 16 is positioned directly above and very close to the patient. The detector 16 is mounted in a yoke 18, cantilevered from a suspended member 20 mounted to a vertical column structure 22. The vertical position of the detector 16 is controlled by a suspension system contained within the structure 22, which operates a ⅛ inch diameter 7×19 strand aircraft quality wire cable 24. The cable 24 extends from the suspended member 20 upward to a follower pulley 26 having a brake control, and downward to a counterpoise device 28. A suitable counterpoise device is shown in U.S. Pat. No. 4,003,552 to Sobolewski and assigned to the assignee of the present invention. Alternative suspension systems could incorporate drive motors, transmissions and pulleys to provide the tensile force of cable 24. The suspension system could also incorporate a sprocket-driven chain or a variety of other configurations to provide a tensile force to the suspended member 20. The invention is compatible with any suspension system in which the member 20 is suspended by an upward tensile force.

The safety catch apparatus 29 of this invention is roughly shown by the dashed lines of a catch block 30 adapted for slideable engagement with a vertically supported stationary bar 32. The member 20 has a vertical aperture 34, also adapted to receive the stationary bar 32. The bar 32 is fixedly attached to the vertical column structure 22, as shown at 36, and remains stationary throughout the operation of the system. The cable 24 is attached to member 20 by way of catch block 30, which is constrained within an inner chamber 38 of the member.

Figure 2:
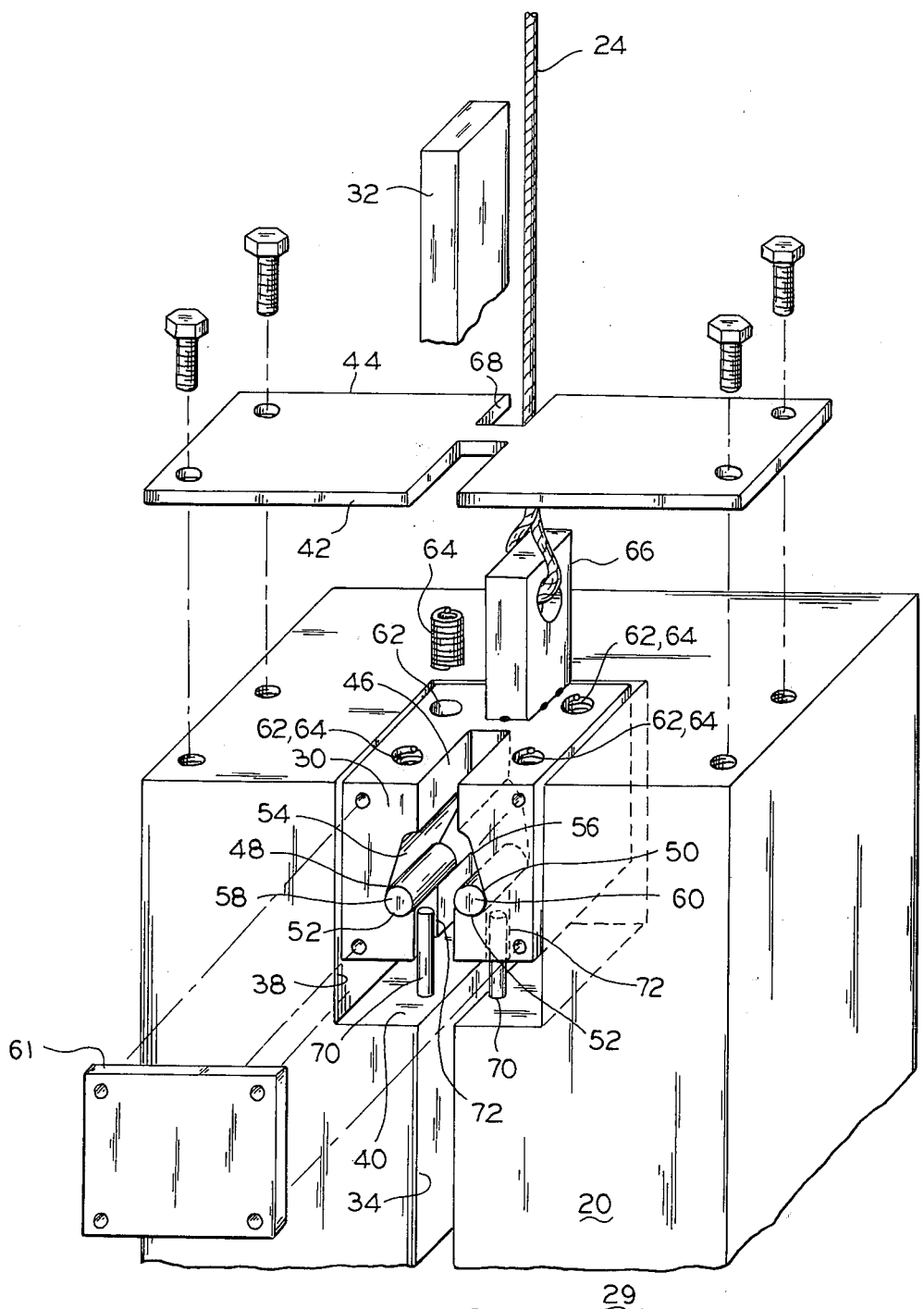
FIG. 2 is an enlarged exploded view of the invention as designated by arrows 2—2 of FIG. 1.
Figure 3:
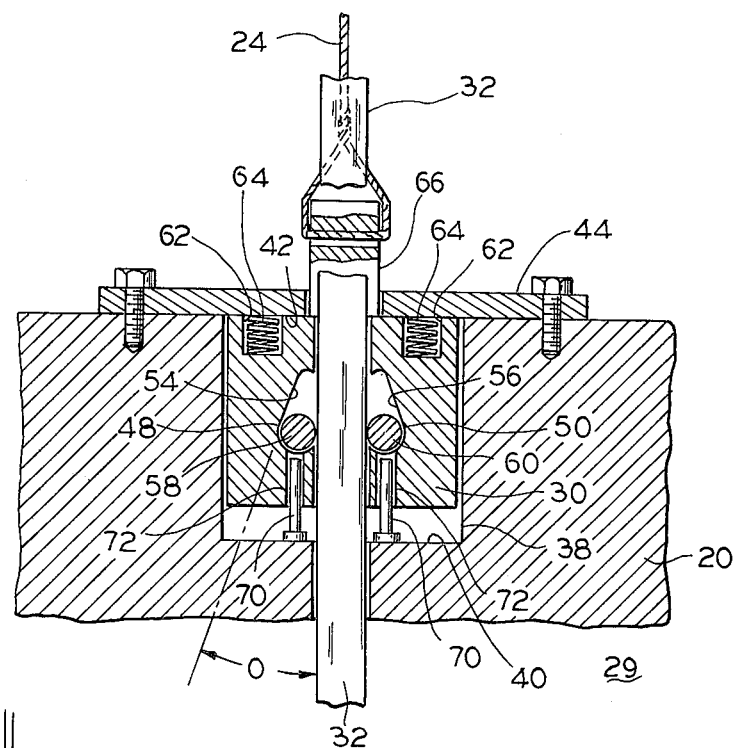
FIG. 3 is a sectional view of the safety catch apparatus in the ready position with tension on the suspension system.
Figure 4:
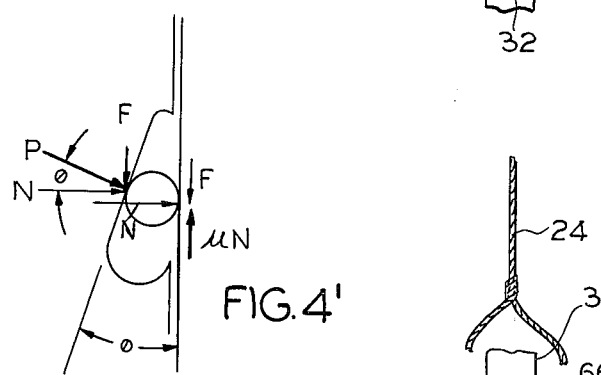
FIG. 4 is a sectional view similar to FIG. 3 showing a suspension system failure and the safety catch apparatus engaged to support the member and also showing the forces acting on the apparatus.
Figure 4:
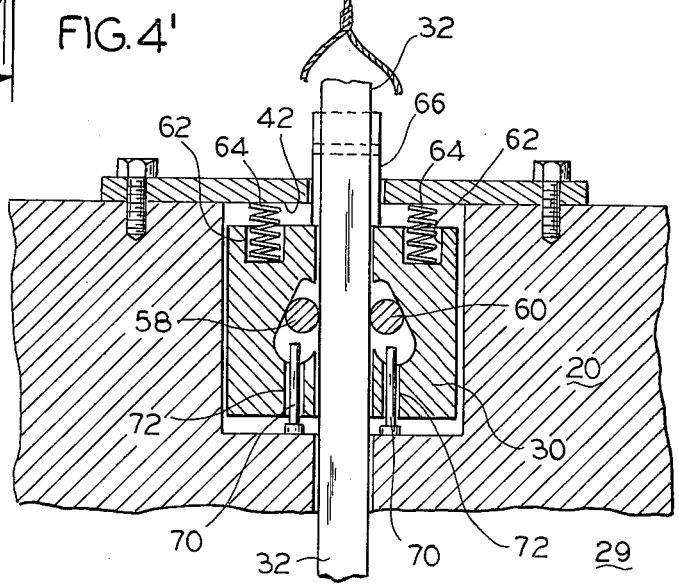

Referring now to FIGS. 2, 3 and 4, there are shown the details of the preferred embodiment of the safety catch apparatus 29 of this invention. The safety catch apparatus functions within the inner chamber 38 of the suspended member 20. The inner chamber 38 is shown as a generally rectangular cavity in the upper/forward section of member 20 and communicates with the vertical aperture 34 in the member. Inner chamber 38 has a lower surface 40 and an upper surface 42. As shown, the upper surface 42 is provided by a top plate 44 attached to member 20.

The catch block 30 is carefully sized to fit within chamber 38 and adapted to have very little lateral motion, but having clearance for vertical movement (of approximately 0.25 inches) between the upper and lower surfaces of the chamber. The catch block has a vertical slot 46 adapted for slideable engagement with the stationary bar 32. The vertical slot 46 has open recesses 48 and 50 in the opposite side walls of the slot. Each recess 48 and 50 has a base 52 and an inner wall 54 and 56 angulated toward the vertical slot. Each open recess 48 and 50 contains a roller 58 and 60 which freely rests in the base 52. Suitable rollers are provided by standard dowel pins 0.2502 inch in diameter by 0.625 inches long. Smooth dowel pins are used in this preferred embodiment, but knurled dowel pins may improve performance in some applications. The recess bases 52 are semi-cylindrical in shape and located so that the rollers 58 and 60 in the bases are adjacent to, but do not extend into, slot 46 and do not contact the stationary bar 32. The inner walls 54 and 56 of the recesses are tangent to the base 52 and have flat surfaces angulating toward the vertical slot 46 at an angle of approximately 9°. In alternative embodiments, any angulation of less than 12° will provide the safety catch locking action; however, in this preferred embodiment, the 9° angulation was found to provide the best locking action over the shortest free fall distance, as will be discussed later. The catch block 30 can be produced from suitable tool steel material. The rollers are confined within the recesses by a suitable cover 61 attached to catch block 30.

The upper surface of catch block 32 contains a plurality of counterbores 62 adapted to receive compressable elastic members, such as actuator springs 64. The actuator springs 64 act as the sensor and the initiating force for the safety catch apparatus. In this embodiment, the actuation force is selected to be at a tensile load 200 pounds or less. The quantity and spring rate of the springs 64 are selected corresponding to the sensitivity to loss of tension that is desired for the safety catch actuation. Catch block 30 also has a vertical lug 66 which extends through an opening 68 in the top plate 44. Cable 24 of the suspension system is connected to the catch block at lug 66. Once tensile force is applied to cable 24, the catch block 30 is drawn up to the upper surface 42 and the interposed actuator springs 64 are compressed into the counterbores 62 providing a vertical clearance between the catch block and the lower surface 40. Actuator pins 70 are interposed between the catch block 30 and the lower surface 40 and are positioned directly beneath the base 52 of each recess 48 and 50. The catch block has corresponding vertical openings 72 at the base 52 of each recess to allow passage of each pin 70 to contact the respective roller. As shown particularly in FIG. 3, the entire suspended member 20 is supported by catch block 30 which is supported by cable 24 and the safety catch apparatus 29 is in the ready position.

Once the tensile force is removed or decreased from cable 24, the compressed actuator springs 64 will immediately force catch block 30 downward and over the actuator pins 70. The actuator pins 70 will cause the rollers 58 and 60 to be advanced along the respective inner wall 54 and 56, whereby roller 58 immediately becomes wedged between the inner wall 54 and the stationary bar 32, and roller 60 immediately becomes wedged between inner wall 56 and stationary bar 32, thereby locking the catch block 30 to the stationary bar 32. At this time, the member has dropped less than 0.25 inches and the entire weight of the suspended member 20 is supported by the catch block 30, which is suspended by stationary bar 32, as shown particularly in FIG. 4.

In this preferred embodiment, the movable catch block, actuator springs 64 and actuator pin 70 are incorporated to provide a biasing means to generate relative motion between the roller 58 and the recess 48. Once roller 58 is advanced into contact with bar 32, the relative movements draw the roller tightly into the inner wall 54 and does not require further advancement by the pin 70. A variety of other well known mechanisms could be incorporated to generate the relative motion which advances the roller into the stationary bar.

In this nuclear imaging example, a failure of one of two torsion springs (not shown) in the counterpoise system 28 will reduce the tensile load by one-half and the suspended member will drop. Therefore, it is desired that the safety catch be automatically engaged at any tensile load of less than two hundred pounds. A corresponding actuating force of two hundred pounds is provided by four coiled actuator springs 64 each compressed approximately 0.10 inches to each produce a fifty pound load. A variety of spring configurations having spring rates and compressed lengths to fit within counterbore 62 and produce an average force of two hundred pounds will sufficiently actuate the safety catch.

Figure 6:
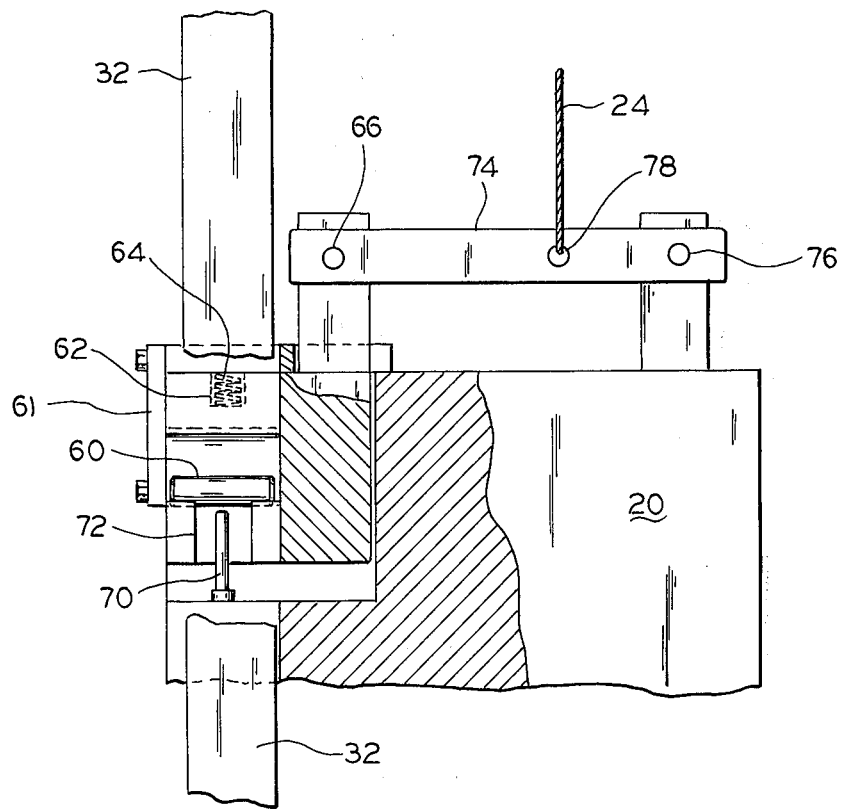
FIG. 6 is a side elevation view of another embodiment of the invention.

Referring to FIG. 6, it is shown that the tensile load which will permit expansion of the actuator springs 64 can be varied by utilizing a linking member 74 to provide a mechanical advantage. Linking member 74 is generally horizontally disposed and has one end pivotally attached to catch block lug 66 and has the other end pivotally attached to a suspended member lug 76. The cable 24 of the suspension system is attached at a desired location 78 along the span of linking member 74. A mechanical advantage is produced which is equal to the ratio of the total length of the linking member 74 divided by the length of the linking member between location 78 and attachment lug 76. The mechanical advantage provided by the linking member 74 can be used to reduce the forces required by actuator springs 64 in an initial design or to adjust the attached location 78 to calibrate the actuation force to a predetermined tensile load.

Referring to FIG. 4', the angle of the inner wall can be analyzed. The angle $\theta$ of the inner wall, such as 54, is extremely critical to the locked engagement of the catch block 30 and to the free fall drop of the catch block prior to locked engagement. It is readily shown that the wedging action is produced by a side load "P," having a vertical downward component "F" and a horizontal component "N" exerted on roller 58 and transmitted as a horizontally tangent force equal to N on stationary bar 32 and a downward, sliding force equal to F. In order for the positive engagement to lock the catch block 30, the downward force F must be exceeded by the frictional force between the roller 58 and the bar 32. Where "$\mu$" represents the value of the coefficient of sliding friction, the frictional force can be designated as $\mu N$. This relationship can be expressed symbolically as follows:

$$F = P \sin \theta$$

$$N = P \cos \theta$$

for lockup, $$F < \mu N$$

or, $$P \sin \theta < \mu P \cos \theta$$

and reduces to, $$\mu > \tan \theta$$

Therefore, the requirement for locked engagement is independent of the load and is determined by the coefficient of friction $\mu$ and the angle $\theta$ of the inner wall. Assume a reasonable upper limit for the coefficient of friction between a smooth steel dowel pin, such as 58, and a bar of cold rolled steel, such as stationary bar 32, to be approximately 0.215. Solving for the arc tangent of 0.215 results in an angulation of less than 12° on the inner wall to assure lockup of the apparatus. It is readily shown that the smaller the angle $\theta$, the smaller the downward component F and the greater the frictional force $\mu N$, and the greater is the assurance of locked engagement. The free fall distance, however, is increased due to the additional travel required by the rollers. And similarly, the greater the angle $\theta$, the shorter the free fall distance prior to engagement, but the lesser the assurance of lockup. It is, therefore, a design compromise to balance the allowable free fall distance to the required lockup, with the angle $\theta$ of the inner wall 54, and the frictional force $\mu N$. It was estimated that the least favorable $\mu$ would be approximately 0.155, which corresponds to locked up engagement at 9° angulation.

The above analysis was confirmed by laboratory evaluation in which a series of catch blocks (30), which had inner walls (54 and 56) angulated at 12°, 9°, 7°, and 5° and were tested with a load of 300 pounds and a simulated suspension system failure.

The tests included 10 tests each, in which the cable (24) was released with the following free fall drops (in inches):

$\theta = 12°$ with clean and dry catch block and bar; did not lockup, indicating a $\mu$ lower than 0.21, and failed the test.

$\theta = 9°$, clean and dry block and bar; shortest drop=0.163, longest drop=0.212, average drop=0.191 inches.

$\theta = 7°$, clean and dry block and bar; shortest drop=0.190, longest drop=0.245, average drop=0.219 inches.

$\theta = 5°$, clean and dry block and bar; shortest drop=0.273, longest drop=0.321, average drop=0.298 inches.

$\theta = 9°$, with bar liberally lubricated with "3in-1" oil; shortest drop=0.198, longest drop=0.224, average drop=0.211 inches.

$\theta = 9°$, with block and bar coated with Shell bearing grease; shortest drop=0.201, longest drop=0.232, average drop=0.214 inches The inner wall angulation of 9° was selected for the preferred embodiment to assure that the safety catch apparatus would have a free fall drop less than 0.250 inches prior to locked engagement under the worst expected operating conditions.

Figure 5:
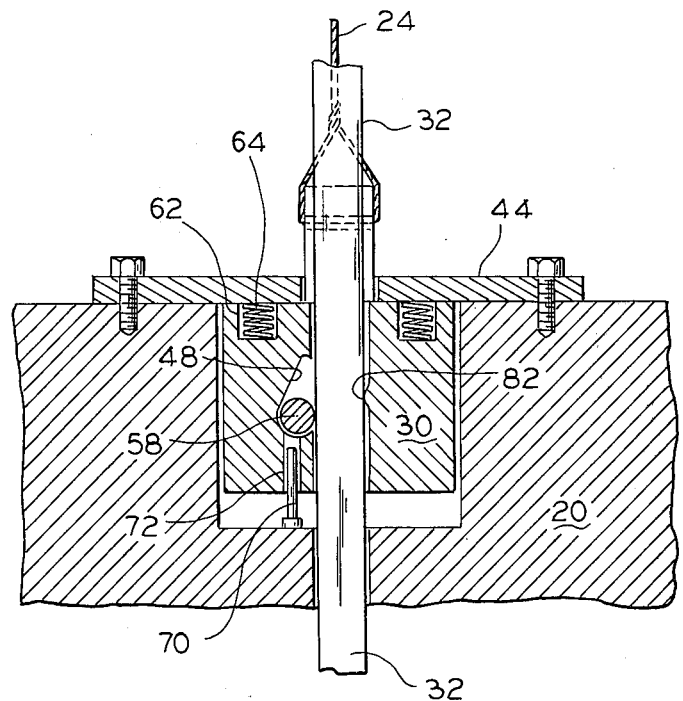
FIG. 5 is a sectional view of another embodiment of the invention.

Referring now to FIG. 5, there is shown another embodiment of a safety catch apparatus 80. The components and operation of the safety catch apparatus 80 are similar to safety catch apparatus 29, as shown and discussed in reference to FIG. 3. The obvious distinction is that this embodiment includes only one open recess 48, one roller 58, and one actuator pin 70. As previously discussed, the theoretical operation of the safety catch apparatus is not dependent upon load. Therefore, the one roller embodiment would perform equally as well as a multiple roller embodiment. In actual operation, however, the clearances between the vertical slot 46 in catch block 30 and the stationary bar 32 operate away from the single roller 58 during engagement and results in a longer free fall drop prior to locked engagement of the apparatus. Catch block 30 can be produced having a raised portion 82 on the side wall of slot 46 opposite the recess 48 to facilitate the locking engagement of the apparatus. This simpler embodiment is a lower cost safety catch apparatus for applications where free fall drop prior to locked engagement is somewhat less critical.

In all embodiments of the safety catch apparatus, the device can be readily reset and is reusable over repeated engagements. Once the failed suspension system has been repaired and a tensile force is reapplied to cable 24, the catch block 30 is raised and removes the loading force from the rollers. The rollers readily return to the base 52 in the respective open recess and remain in the ready position for a future suspension system failure.

The present invention provides a simple, inexpensive safety catch apparatus which allows a minimal drop of the suspended member upon failure of the suspension system. The invention also provides a safety catch apparatus which can be actuated by a partial release in tensile load and which can be readily reset and reactuated.

While specific embodiments of the present invention have been illustrated and described herein, it is realized that modifications and changes will occur to those skilled in the art. It is, therefore, to be understood that the appended claims are intended to cover all such modifications and changes as fall within the true spirit and scope of the invention.

The invention claimed is:

1. A safety catch apparatus for retaining a suspended member in the event that the suspension system fails, comprising:
   a. a generally vertically supported stationary bar;
   b. said suspended member having an aperture adapted to receive said stationary bar;
   c. said suspended member further including an inner chamber having an upper and a lower surface communicating with said aperture;
   d. a catch block sized to fit within said chamber and including a vertical slot adapted for slideable engagement with said stationary bar, said suspended member with said catch block thus being constrained to jointly move along said stationary bar;
   e. said vertical slot having at least one open recess in the sides thereof, each said recess having a base and an inner wall angulated toward said slot;
   f. a roller which freely rests in the base of each said recess, each said roller and said base being sized so that the roller is adjacent to, and spaced from, said stationary bar;
   g. means for generating relative motion between each said roller and said catch block in the event of a suspension failure whereby each said roller becomes wedged between said inner wall and said stationary bar such that said stationary bar supports said suspended member.

2. The safety catch apparatus as recited in claim 1 wherein said vertical slot has two said open recesses on opposite sides of said slot.

3. A safety catch apparatus for retaining a suspended member in the event that the suspension system fails, comprising:
   a. a generally vertically supported stationary bar;
   b. said suspended member having an aperture adapted to receive said stationary bar;
   c. said suspended member further including an inner chamber having an upper and a lower surface communicating with said aperture;
   d. a catch block sized to fit within said chamber and adapted for vertical movement between said upper and lower surfaces of said chamber and including a vertical slot adapted for slideable engagement with said stationary bar;
   e. means for connecting the suspension system to said catch block so that the suspended member with said catch block jointly move along said stationary bar;
   f. said vertical slot having open recesses in opposite sides thereof, each said recess having a base and an inner wall angulated toward said slot;
   g. a roller which freely rests in the base of each said recess, each said roller and said base being sized so that the roller is adjacent to, and spaced from said stationary bar;
   h. biasing means between said catch block and a surface of said chamber which stores energy once tensile force is applied to said catch block by the suspension system;
   i. actuator pins interposed between said catch block and the lower surface of said chamber, said pins positioned beneath the base of each said recess of said catch block;
   j. said catch block having vertical openings at the base of each said recess adapted to receive said pins; and
   k. whereby, if the tensile force is removed from said catch block, said biasing means will immediately force said catch block downward over said pins which will advance each said roller along the inner wall of said recess whereby said roller immediately becomes wedged between said catch block and said stationary bar such that said stationary bar supports said suspended member.

4. A safety catch apparatus for a medical diagnostic device having a suspension system and a heavy suspended member positioned above a patient, said safety catch apparatus for retaining the suspended member in the event that the suspension system fails, comprising:
   a. a generally vertically supported stationary bar;
   b. said suspended member having an aperture adapted to receive said stationary bar;
   c. said suspended member further including an inner chamber having an upper and a lower surface communicating with said aperture;
   d. a catch block sized to fit within said chamber and including a vertical slot adapted for slideable engagement with said stationary bar, said suspended member with said catch block thus being constrained to jointly move along said stationary bar;
   e. said vertical slot having at least one open recess in the sides thereof, each recess having a base and an inner wall angulated toward said slot;
   f. a roller which freely rests in said base of each said recess, each said roller and said base being sized so that the roller is adjacent to, and spaced from, said stationary bar;

g. means for generating relative motion between each said roller and said catch block in the event of a suspension failure whereby each said roller becomes wedged between said inner wall and said stationary bar such that said stationary bar supports said suspended member.

5. The safety catch apparatus, as recited in claim 4, further comprising:
   a. means for connecting the suspension system to said catch block;
   b. said catch block adapted for vertical movement between said upper and lower surfaces of said inner chamber;
   c. said vertical slot has two said open recesses on opposite side thereof;
   d. actuator springs interposed between said catch block and the upper surface of said chamber which compress once tensile force is applied to said catch block by the suspension system;
   e. actuator pins interposed between said catch block and the lower surface of said chamber, said pins positioned beneath the base of each said recess of said catch block;
   f. said catch block has vertical openings at the base of each said recess adapted to receive said pins; and
   g. whereby, if the tensile force is removed from said catch block, said compressed springs will immediately force said catch block downward over said pins which will advance each said roller along the inner wall of said recess whereby said roller immediately becomes wedged between said catch block and said stationary bar such that said stationary bar supports said suspended member.

6. The safety catch apparatus, as recited in claim 3, 4 or 5 wherein said means for connecting the suspension system to said catch block further comprises:
   a generally horizontally disposed linking member having one end pivotally attached to said catch block and having the other end pivotally attached to said suspended member; and
   the suspension system attached at a desired location along the length of said linking member whereby a mechanical advantage is produced, thereby reducing the tensile force at which said apparatus will actuate.

7. The safety catch apparatus as recited in claim 1, 2, 3, 4 or 5 wherein each said recess has said inner wall angulated toward said slot at an angle of less than 12°.

8. The safety catch apparatus as recited in claims 1, 2, 3, 4 or 5 wherein each said recess has said inner wall angulated toward said slot at an angle of from 5° to 9°.

9. The safety catch apparatus as recited in claims 1, 2, 3, 4 or 5 wherein each said recess has said inner wall angulated toward said slot at an angle of 9°.

* * * * *